United States Patent [19]

Shoher et al.

[11] Patent Number: 4,742,861

[45] Date of Patent: May 10, 1988

[54] METHOD AND MATERIAL FOR DENTAL STRUCTURES

[76] Inventors: Itzhak Shoher, 50 Shlomo-Hamelech St., Tel-Aviv, Israel, 64386; Aharon E. Whiteman, 13 J. L. Perez St., Petach-Tikvah, Israel, 49206

[21] Appl. No.: 937,011

[22] Filed: Dec. 2, 1986

Related U.S. Application Data

[63] Continuation-in-part of Ser. No. 723,063, Apr. 7, 1985.

[51] Int. Cl.$^4$ ............................................. B22D 19/10
[52] U.S. Cl. ..................................... 164/80; 164/92.1; 164/97; 419/27
[58] Field of Search .................... 164/97, 80, 92.1; 419/26, 27, 47

[56] References Cited

U.S. PATENT DOCUMENTS 3,502,466  3/1970  Vickery .................... 419/27

FOREIGN PATENT DOCUMENTS 0052922  6/1982  European Pat. Off. ............ 419/27

Primary Examiner—Kuang Y. Lin

[57] ABSTRACT

A dental material and method for forming, reinforcing or repairing a dental restoration comprising a combination of a high fusing temperature metal component in a major proportion and a low fusing temperature component in a minor proportion. A binder may be added to form a putty-like consistency. The dental material is molded into a predetermined shape and heat treated at a temperature which will substantially melt the low fusing metal components but below the melting temperature of the high fusing metal component for forming a porous, sponge-like mass of interconnected particles of the high fusing temperature metal component. A filler material having a low melting temperature is then added to the porous mass and the mass is again treated to form a solid mass.

11 Claims, No Drawings

METHOD AND MATERIAL FOR DENTAL STRUCTURES

This application is a continuation-in-part of U.S. Ser. No. 723,063, filed Apr. 7, 1985, and relates to a method and material for reinforcing a dental metal structure in forming or repairing a dental restoration.

BACKGROUND OF THE INVENTION

In crown and bridge prosthodontics, a wide diversification of retainers and pontics can be used in various combinations for constructing a bridge. A ceramic to metal restoration uses a framework of metal as reinforcement for the crown and bridge upon which is applied a fired on coating of a ceramic material such as porcelain. The framework of metal may either be cast or formed from prefabricated units of preformed copings and pontics. In accordance with present practice, a framework may be altered by soldering but otherwise cannot be modified or reinforced without involving investment and casting operations. Present practice is limited because of the unavailability of commercial materials with which to build up or extend the framework. To reinforce a framework without investment and casting requires adding material to the framework which upon heat treatment will become an integral part of the framework. The material must be capable of being molded into a desired shape and must be self-supporting in the molded configuration as well as capable of retaining the shape in which it was molded under heat treatment. To be able to shape the material into a desired configuration, the material should be relatively soft and workable. Under heat treatment, the material should solidify into a rigid mass of metal without losing the shape in which it was molded prior to heat treatment. The material should fuse to the metal framework and should have a hardness characteristic of at least equal but preferably greater than the hardness of the material before heat treatment.

Such a material could be used, for example, to build up a cervical shoulder around a retaining member at the gingival margin without the need for investment or casting. For example, a finishing shoulder can be formed around a prefabricated metal coping which was preformed without a shoulder margin. The finishing shoulder can be molded into any shape by the dental technician. Likewise, the material can be used to build metal cusps upon a metal coping before ceramic porcelain is added to provide buccal and/or lingual cusp reinforcement. The material may also be used to strengthen joints at predetermined locations in the framework or for general bridgework repair. The latter is, at present, relatively impossible. Heretofore, the dentist and dental technician were essentially limited to use of cast dental structures and to materials useful as solders or fluxes. Neither the conventional solder nor flux is capable of being molded into a self-supporting configuration nor is either material capable of retaining a shape under heat treatment. Soldering alloys are, in fact, designed to melt and flow freely under the heat of a soldering flame and function to join metals by fusion. A flux is a non-oxidizing agent.

In Applicants parent patent application U.S. Ser. No. 723,063, a dental material composition is disclosed for reinforcing a metal framework incorporating a high fusing temperature precious metal component and a low fusing temperature precious metal component. The high fusing component is in a proportion by volume of from 1-15% of the total composition in the dental material. The material is heat treated at a temperature below the melting temperature of the high fusing temperature metal component to cause the low fusing temperature component to substantially melt and flow around the high fusing temperature component. The dental material solidifies into a rigid mass in response to heat treatment while retaining the shape it was given prior to heat treatment. However, during heat treatment, the mass shrinks as it solidifies. The effect of shrinkage although undesirable, is a necessary characteristic of the foregoing dental material to avoid the formation of voids and air bubbles during heat treatment. Nevertheless some shrinkage can be tolerated for most applications. Likewise, extra material may also be added to compensate for shrinkage but adding extra precious metal is an expensive solution and is not very practical.

SUMMARY OF THE INVENTION

The method and material of the present invention forms a mass which retains its shape but does not suffer any shrinkage from heat treatment and is accordingly ideal for use in dental procedures where shrinkage cannot be tolerated. In addition, the present method results in very little waste of precious metal and is thus highly cost effective.

The method of the present invention is primarily useful for reinforcing a metal structure in a dental restoration and comprises forming a material composition of metal particles composed substantially of a high fusing temperature metal component and a low fusing temperature component with the low fusing temperature component being in a minor proportion relative to the high fusing temperature component; adding the material composition to the dental structure to be reinforced; molding the material composition into a predetermined shape; heat treating the material composition at a temperature below the melting temperature of said high fusing temperature component and at a temperature level sufficient to cause substantial melting of said low fusing temperature component for forming a porous sponge like mass adapted to fuse to the dental structure; adding particles of a low melting temperature filler to said porous sponge like mass and heat treating said filler particles to cause the filler particles to melt into the sponge like mass whereby a solid reinforced structure is formed. The filled in solidified mass may then be further shaped if desired.

A ceramic material may be applied to the reinforced structure in a conventional fashion and fired in a furnace to form a ceramic to metal dental restoration.

The reinforcing material of the present invention comprises a metal composition including a substantial proportion of particles of high fusing temperature metal having a melting temperature above at least about 1300° C. with such high fusing temperature metal particles being below 100 microns in size and with said composition having a minor proportion of a low fusing temperature metal which is adapted to melt upon heat treatment at a temperature below said high fusing melting temperature and preferably below 1200° C.

DESCRIPTION OF THE PREFERRED EMBODIMENTS

Broadly the dental material of the present invention is a composition of metal particles which can be molded upon heat treatment into a desired self-supporting shape for forming a dental reinforcement in forming or repairing a dental restoration. The dental material of the present invention will fuse to a dental framework upon heat treatment and retain the shape in which it was molded. The method of the present invention permits the dental material to be formed into a solid mass without suffering any shrinkage. The dental material is composed of a composition of metal particles containing a high fusing temperature precious metal component of a single metal or a metal alloy. The high fusing temperature precious metal particles should be sized preferably no greater than about 100 microns and should represent the major constituent of the total composition of the dental material. The dental material should preferably also include a minor proportion of a low fusing temperature precious metal component of a single metal or metal alloy in the form of particles or clad to the particles of the high fusing temperature precious metal. The melting temperature of the high fusing temperature metal component should be substantially higher than the melting temperature of the low fusing temperature metal component and substantially higher than the temperature at which the material is heat treated. Under heat treatment, the low fusing temperature component melts to fuse the high temperature particles together at its points of contact to form a porous sponge-like structure which retains the shape it is given prior to heat treatment.

A binder or other suitable carrying vehicle may be added to the composition of metal particles in forming the dental material of the present invention to give the material a paste or putty-like constituency. This should make the material easier to work with. A binder should be selected which will volatize during heat treatment without leaving a residue. Any suitable organic resinous or synthetic resinous material is acceptable such as, for example, ethylene or polyethylene glycol. In addition to a binder a flux such as borax may be added to form the dental material of the present invention. The flux eliminates the formation of oxides.

The composition of metals forming the dental material should be bio-compatible for use in the mouth. Accordingly, precious metals and precious metal alloys are preferred although not essential. The precious metals may also be used in combination with non-precious metals. In the foregoing embodiment of the invention, the high fusing temperature metal composition is primarily composed of a combination of from 0to 100% platinum and from 100 to 0% palladium with or without other minor constituents such as gold. Gold may be added to the high fusing temperature metal composition to increase the affinity of the particles of the high fusing temperature component to the low fusing temperature component. The particles of the low fusing temperature metal is preferably composed of a gold alloy with gold as the major constituent or entirely of gold. The preference for gold as the major constituent of the low fusing component is based on its known characteristics of workability, non-oxidizing property and its color.

The size of the particles of the high fusing temperature metal component is an important characteristic of the present invention. Best results achieved when the largest particle size of the high fusing temperature component is below about 100 microns and preferably below 74 microns. The high fusing temperature component particles should also be larger in size than the particle size of the low fusing component. The high fusing temperature component should be at least equal to the particle size of the low fusing component but preferably about 5-10 times larger than the particle size of the low fusing component. When the low fusing component is cladded to the particles of high fusing particles the latter should also be much larger in size based upon relative thicknesses between the clad components. The shape of the particles of the high fusing component is considered important to the present invention but is not a critical characteristic. Irregularly shaped particles in the form of flakes appear to function best. An irregular shape allows the particles to form a mesh or open interlocking network of particles. The low fusing metal component fuses the particles of the high fusing temperature at the contact points in the open network to form a porous sponge-like mass under heat treatment. Any shape is acceptable including a spherical shape although strips and irregularly contoured shapes particularly a crescent shape is preferred.

Although the material of the present invention is a composition of metal particles, the method of forming the particles is not critical to the present invention and as stated earlier, the low fusing component particles may be cladded to the high fusing component particles to form a composite of a high fusing temperature component and a low fusing temperature component. The cladded particles may have one component totally encapsulating the other or only partially covering one another. Cladded particles may be formed, for example, from multiple layered sheets which may have been laminated. Various other known deposition processes may also be used to form layered sheets or to encapsulate the particles one within the other including, for example, electrodeposition and cathode sputtering. Where the metal particles are cladded to one another the proportion of the high fusing component to the low fusing component in the total composition would be based on the difference in the thickness between the cladded metals. Preferably the thickness of the low fusing component should be in a range of 8 to 15 microns for reasons which will be discussed hereafter.

The method of the present invention comprises forming a dental material with a high fusing temperature component as heretofore defined preferably in combination with a low fusing temperature component as heretofore defined. The low fusing temperature component is intended to function solely as a soldering agent for fusing the particles of the high fusing temperature metal together at their points of contact upon heat treatment. Accordingly, the high fusing temperature component should constitute a major proportion of the combination of particles of the high and low fusing temperature components and up to about 100 by weight thereof with 50 to 75% by weight being preferred. In fact, the high fusing temperature component may in fact represent 100% of the composition if heat treatment is carried out in combination with the application of pressure to cause the particles of the high fusing temperature component to autogenously fuse together at their contact points. A binder and/or fluxing agent is then added to the dental material before it is applied to the dental structure. A binder may be added as earlier explained to give the dental material a past-like clay constituency which should make the material easier to work with. The dental material is added to a dental structure such as a metal coping or bridge to add reinforcement to the structure at desired specific locations or to extend the structure etc. The dental material may be applied to the structure by a brush or spatula and burnished or molded by hand into a desired shape. The dental structure including the dental material is then heat treated by subjecting it to the flame of a Bunsen burner or by sintering in a furnace at a temperature below the melting temperature of the high fusing temperature component. The melting temperature of the high fusing temperature component should be above about 1300° C. wheras the heat treatment temperature should be carried out at a temperature below about 1200° C. and preferably between about 1025° C. to 1175° C. Heat treatment causes the dental material to form a porous mass of metal in the form of an open network of interconnected metal particles of generally sponge-like appearance which fuses to the dental structure. The porous sponge-like mass of metal retains the shape it was given prior to heat treatment and does not suffer any shrinkage during heat treatment.

After heat treatment particles of filler having a low melting temperature are added to the porous mass of metal and heat treated to cause the filler particles to melt into the sponge-like porous mass whereby a solid reinforced structure is formed. The particles of filler are preferably metal particles of gold. Heat treatment of the filler particles can be carried out at the same heat treatment temperature as originally carried out to form the porous mass. The low fusing temperature in the porous mass was melted during heat treatment to form an alloy with the high fusing metal at the points of contact where the low fusing component solidifies. The metal alloy has a higher melting temperature than the melting temperature of the original low fusing component and accordingly it will not remelt upon renewed heat treatment at the same temperature. Alternatively, filler particles can be selected with a different melting temperature than the original melting temperature of the low fusing metal component. For example, the filler particles can be gold and the low fusing metal a gold alloy or they can both be pure gold or gold alloys. Other metals may also be used. Moreover, the porous sponge may be filled with filler particles of a ceramic composition such as porcelain or with a resin or resin filled dental composite material where strength is not required and particularly for repair of a chipped porcelain restoration.

The low fusing metal component may consist of a single metal such as pure gold or an alloy thereof or of more than one metal alloy in combination. When the low fusing component is plated onto the particles of the high fusing component to form cladded particles, it is important that the thickness of the low fusing component be small relative to the thickness of the high fusing component. The preferred thickness is between 8-15 microns. The high fusing metal component may be a composition of gold, platinum and palladium with minor additions of other constituent elements with the combination of palladium and/or platinum being the major constituent.

It should be understood that the invention is not to be construed as limited to any given application for the material. The material may, for example, be added to a dental framework after the porcelain has been fired. If, for example, a crown is too short at the margin this material may be used to extend the crown. Accordingly, the word "reinforce" is not to be given a narrow interpretation but is instead to be given a much broader definition so that it specifically encompasses the idea of increasing the size and physical dimensions of the framework by simply adding to or extending the framework. In the same manner the material of the present invention may be used to fill a space between adjacent teeth upon which a fired on ceramic veneer may be applied, if desired.

What is claimed is:

1. A method for forming reinforcing or repairing a dental restoration comprising forming a material composition of metal particles composed substantially of a high fusing temperature metal component and a low fusing temperature component with the low fusing component being in a minor proportion relative to the high fusing temperature component; adding the material to the dental restoration to be reinforced or repaired; molding the material composition into a predetermined shape; heat treating the material composition at a temperature below the melting temperature of said high fusing temperature metal component and at a temperature level sufficient to cause substantial melting of said low fusing temperature component for forming a porous sponge-like mass of interconnected particles particles of said high fusing temperature metal component; adding particles of a low melting temperature filler to said porous sponge-like mass of metal and heat treating said filler particles to cause said filler particles to melt into the sponge-like mass whereby a solid reinforced structure is formed.

2. A method as defined in claim 1 wherein said material composition of metal particles comprises precious metals and a binder.

3. A method as defined in claim 2 wherein said high fusing temperature metal component comprising particles selected from the class consisting of platinum and palladium.

4. A method as defined in claim 3 wherein the melting temperature of said high fusing temperature component is above about 1300° C. and wherein said heat treating temperature is below about 1200° C.

5. A method as defined in claim 4 wherein said low fusing temperature component comprises gold.

6. A method as defined in claim 5 wherein said high fusing temperature metal particles are of a size no greater than about 100 microns.

7. A method as defined in claim 6 wherein said filler comprises particles of a metal or metal alloy.

8. A method as defined in claim 7 wherein said filler particles comprise gold.

9. A method as defined in claim 1 wherein said filler comprises a ceramic composition or a resin or a resin filled dental composite material.

10. A method as defined in claim 9 wherein said ceramic is porcelain.

11. A method as defined in claim 3 wherein said high fusing metal component comprises up to about 50—75% by weight of the combination of high and low fusing metal components.

* * * * *